United States Patent
Hankoua et al.

(10) Patent No.: US 11,154,023 B2
(45) Date of Patent: Oct. 26, 2021

(54) **SYSTEM FOR RAPID, ROBUST, AND EFFICIENT IN VITRO MASS PROPAGATION OF *MISCANTHUS* × *GIGANTEUS***

(71) Applicants: Bertrand B. Hankoua, Dover, DE (US); Ayalew Ligaba Osena, Dover, DE (US)

(72) Inventors: Bertrand B. Hankoua, Dover, DE (US); Ayalew Ligaba Osena, Dover, DE (US)

(73) Assignee: Delaware State University, Dover, DE (US)

( * ) Notice: Subject to any disclaimer, the term of this patent is extended or adjusted under 35 U.S.C. 154(b) by 0 days.

(21) Appl. No.: 16/745,883

(22) Filed: Jan. 17, 2020

(65) Prior Publication Data

US 2020/0154661 A1 May 21, 2020

Related U.S. Application Data

(63) Continuation of application No. PCT/US2018/043130, filed on Jul. 20, 2018.

(60) Provisional application No. 62/534,935, filed on Jul. 20, 2017.

(51) Int. Cl.
*A01H 4/00* (2006.01)
*A01G 20/00* (2018.01)

(52) U.S. Cl.
CPC ............ *A01H 4/005* (2013.01); *A01G 20/00* (2018.02)

(58) Field of Classification Search
CPC . A01H 4/007; A01H 5/12; A01H 4/00; A01H 4/008; A01H 6/46; A01G 2/00
USPC ........................................ 435/420
See application file for complete search history.

(56) References Cited

U.S. PATENT DOCUMENTS

| | | |
|---|---|---|
| 9,055,721 B2 | 6/2015 | Mei et al. |
| 2012/0042569 A1 | 2/2012 | Mei et al. |
| 2013/0111619 A1 | 5/2013 | Sacks et al. |
| 2015/0282431 A1 | 10/2015 | Dreher |

FOREIGN PATENT DOCUMENTS

| | | |
|---|---|---|
| WO | 2008136797 A1 | 11/2008 |
| WO | 2010011717 A2 | 1/2010 |
| WO | 2013186558 A1 | 12/2013 |
| WO | 2014067513 A2 | 5/2014 |

OTHER PUBLICATIONS

Gubisova et al.Enhanced in vitro propagation of Miscanthus × giganteus Industrial Crops abd Products 41 (2013) 279-282.*
Gawel et al. In Vitor Propagation of Miscanthus sinensis HortScience 25(10) 1291-1293. 1990.*
Lewandowski Micropropagation of Miscanthus × giganteus Biotecnology in Agriculture and Forestry vol. 39 1997.*
Dalton Biotchnology of Miscanthus. Biotechnology of Neglected and Underutilized Crops pp. 243-294. Apr. 16, 2013.*
Gawel et al., Hort. Soc., Oct. 1, 1990, vol. 25, No. 10, pp. 1291-1293.
International Preliminary Report on Patentability for International Application No. PCT/US2018/043130, dated Jan. 21, 2020, 7 pages.
International Search Report and Written Opinion for International Application PCT/US2018/043130, dated Oct. 3, 2018, 9 pages.
Xue et al., Renewable and Sustainable Energy Reviews, vol. 49, Sep. 2015, pp. 1233-1246.
Kim, S. et al., "An efficient system for high-quality large-scale micropropagation of Miscanthus x giganteus plants," In Vitro Cell.Dev.Biol.—Plant (2012), 48:613-619.
Kim, H.S., et al., "Miscanthus× giganteus plant regeneration: effect of callus types, ages and culture methods on regeneration competence," GCB Bioenergy (2010), vol. 2, 192-200.

* cited by examiner

*Primary Examiner* — Annette H Para
(74) *Attorney, Agent, or Firm* — RatnerPrestia

(57) ABSTRACT

The present invention provides a longitudinally split immature tiller separated from a rhizome (LSITR), a duster of multiple in vitro shoots (CMIT), a cluster of stem segments containing shoot primordia (CSSSP) and an in vitro tiller of *Miscanthus* x *giganteus* (Giant miscanthus), and their uses in propagating *Miscanthus* x *giganteus* (Giant miscanthus).

11 Claims, 3 Drawing Sheets

SYSTEM FOR RAPID, ROBUST, AND EFFICIENT IN VITRO MASS PROPAGATION OF *MISCANTHUS* × *GIGANTEUS*

CROSS-REFERENCE TO RELATED APPLICATION

This application is a continuation application of International Application No. PCT/US2018/043130, filed Jul. 20, 2018 claiming priority to U.S. Provisional Application No. 62/534,935 filed Jul. 20, 2017, the entire disclosure of which is incorporated herein by reference in its entirety for all purposes.

REFERENCE TO U.S. GOVERNMENT SUPPORT

This invention was made with government support under Grant Nos. 2011-38821-30974 and 2014-33821-22417 by the National Institute of Food and Agriculture (NIFA). The United States has certain rights in the invention.

FIELD OF THE INVENTION

The invention relates generally to in vitro mass propagation of *Miscanthus* x *giganteus*.

BACKGROUND OF THE INVENTION

The *Miscanthus* genotype with the greatest biomass potential to date is *Miscanthus* x *giganteus* (Giant miscanthus), a sterile hybrid of *M. sacchariflorus* and *M. sinensis* parentage. Giant miscanthus has been proposed for use in the United States in combined heat and power generation. It is also a leading candidate feedstock for cellulosic ethanol. Although it is widely touted for cellulosic ethanol, Giant miscanthus has traits that likely make Giant miscanthus better suited for thermochemical conversion processes over biological fermentation under existing technology. The main feature distinguishing Giant miscanthus from other biomass crops is its high lignocellulose yields. U.S. Research has shown dry matter yields from 10 to 15 tons per acre, and some cases 20 tons per acre. In the U.S., Giant miscanthus can yield more annual biomass than any other major biomass crop and has a much broader growing range. Based on average yields seen in many trials in the U.S., Giant miscanthus has the potential to supply all the advanced biofuel required under the Energy Independence and Security Act (2007) using only the same land area currently devoted to producing corn grain ethanol. This means that Giant miscanthus could meet biofuel goals without bringing new land into production or displacing food supply. Giant miscanthus is adapted to many soil conditions, including marginal land, but is most productive on soils well suited for corn production. Planting technology such as limited planting material and limited planting equipment is one of the major limitations to large scale economic expansion of Giant miscanthus production in the U.S. for biopower and feedstock for biofuels and green chemicals production. Because Giant miscanthus has three sets of chromosomes and an uneven chromosome number, the chromosomes do not divide evenly during meiosis, leading to non-viable gametes, and hence to sterile seed. This is advantageous because it limits the capacity of Giant miscanthus to spread unintentionally from seed, but it significantly complicates planting of new fields. In addition to lacking the ability to reproduce from seeds, the rhizome structure of Giant miscanthus spreads very slowly, thus minimizing vegetative spread. Since Giant miscanthus produces no seeds, it must be reproduced and established vegetatively by planting divided rhizome pieces or live plants. This process results in high up-front establishment costs relative to crops established from seed, but comparatively reduced costs over the lifetime of the stand. This costs of Giant miscanthus production are front loaded with planting material alone costing between $1,000 and $10,000 per acre. One alternative to address this prohibitive cost of planting materials could be the importation of massive number of cheap rhizomes from Europe. Unfortunately, Giant miscanthus cannot be imported from Europe in any meaningful quantities due to current quarantine restrictions imposed by the USDA. Because Giant miscanthus is a relative of sugarcane, it could conceivably harbor diseases that would threaten the U.S. sugarcane industry. Imported rhizomes must be monitored in quarantine greenhouses for three years before release, a costly process that effectively eliminates importation.

Therefore, development of an alternative, and cost-effective approach for asexually propagating this major energy crop as a strategy to address these production challenges is among many prerequisites to accelerate commercial development of cellulosic biofuels, biopower, biobased, and green chemicals production from this important and high yielding feedstock.

SUMMARY OF THE INVENTION

The present invention provides a longitudinally split immature tiller separated from a rhizome (LSITR), a cluster of multiple in vitro shoots (CMIT), a cluster of stem segments containing shoot primordia (CSSSP), an in vitro tiller of *Miscanthus* x *giganteus* (Giant miscanthus), and the uses or preparation thereof for propagating Giant miscanthus.

A method of generating a cluster of multiple in vitro shoots (CMIT) of *Miscanthus* x *giganteus* (Giant miscanthus) is provided. The method comprises incubating a longitudinally split immature tiller separated from a rhizome (LSITR) of Giant miscanthus in a direct shoot induction medium (DSIM) so that the LSITR develops one or more induced individual shoots (IIS), excising each of the IIS from its base on the LSITR, and incubating each of the excised IIS in the DSIM. A CMIT generated according to this method is provided.

A method of generating a cluster of stem segments containing shoot primordia (CSSSP) of *Miscanthus* x *giganteus* (Giant miscanthus) is provided. The method comprises incubating the CMIT in a direct shoot induction medium (DSIM) so that the CM IT develops multiple in vitro tillers and removing the multiple in vitro tillers from the CMIT so that the CSSSP is generated. Nodes located near the base of each removed in vitro tiller remain within the CSSSP. The multiple in vitro tillers may comprise at least 30 in vitro tillers. A CSSSP generated according to this method is provided.

Another method of generating a cluster of stem segments containing shoot primordia (CSSSP) of *Miscanthus* x *giganteus* (Giant miscanthus) is provided. The method comprises incubating a longitudinally split immature tiller separated from a rhizome (LSITR) of Giant miscanthus in a direct shoot induction medium (DSIM) so that the LSITR develops one or more induced individual shoots (IIS), excising each of the IIS from its base on the LSITR, incubating each of the excised IIS in the DSIM so that a cluster of multiple in vitro shoots (CMIT) is generated, incubating the CMIT in the DSIM so that the CMIT develops multiple in vitro tillers, and removing the multiple in vitro tillers from the CMIT to generate the CSSSP. Nodes located near the base of each removed in vitro tiller remain within the CSSSP. The multiple in vitro tillers may comprise at least 30 in vitro tillers. A CSSSP generated according to this method is provided.

Another method of generating a cluster of multiple in vitro shoots (CMIT) of Miscanthus x giganteus (Giant miscanthus) is provided. The method comprises incubating a cluster of stem segments containing shoot primordia (CSSSP) of Giant miscanthus in a direct shoot induction medium (DSIM) so that the CMIT is generated. A CMIT generated according to this method is provided.

A method of producing multiple in vitro tillers of Miscanthus x giganteus (Giant miscanthus) is provided. The method comprises incubating a cluster of multiple in vitro shoots (CMIT) in a direct shoot induction medium (DSIM) so that the CMIT develops multiple in vitro tillers. The method may further comprise isolating a single in vitro tiller from the multiple in vitro tillers and incubating the single in vitro tiller in the DSIM so that the single in vitro tiller develops multiple in vitro tillers. An in vitro tiller of Miscanthus x giganteus (Giant miscanthus) produced according to this method is provided.

A method of producing multiple in vitro tillers of Miscanthus x giganteus (Giant miscanthus) is provided. The method comprises fragmenting a cluster of stem segments containing shoot primordia (CSSSP) into small clusters of stem segments and incubating each of the small clusters in a direct shoot induction medium (DSIM) so that each of the small clusters of stem segments develops multiple in vitro tillers. Each of the small clusters may comprise at least 5 stem segments. An in vitro tiller of Miscanthus x giganteus (Giant miscanthus) produced according to this method is provided.

The DSIM may comprise maltose, 6-benzylaminopureine (BAP) and α-naphthaleneacetic Acid (NAA).

A longitudinally split immature tiller separated from a rhizome (LSITR) of Miscanthus x giganteus (Giant miscanthus) is provided.

A method of propagating Miscanthus x giganteus (Giant miscanthus) is provided. The method comprises incubating the in vitro tiller of Giant miscanthus of the present invention in a rooting medium so that an in vitro rooted Giant miscanthus plantlet is generated and planting the in vitro rooted plantlet into soil. The rooting medium may comprise maltose, α-naphthaleneacetic Acid (NAA), phytagel, and vancomycin. The rooting medium may have a pH of 5.7.

A method of propagating Miscanthus x giganteus (Giant miscanthus) is provided. The method comprises incubating the cluster of multiple in vitro shoots (CMIT) of Giant miscanthus of the present invention in a rooting medium so that an in vitro rooted Giant miscanthus plantlet is generated and planting the in vitro rooted plantlet into soil. The rooting medium may comprise maltose, α-naphthaleneacetic Acid (NAA), phytagel, and vancomycin. The rooting medium may have a pH of 5.7.

DETAILED DESCRIPTION OF THE INVENTION

Figure 1:
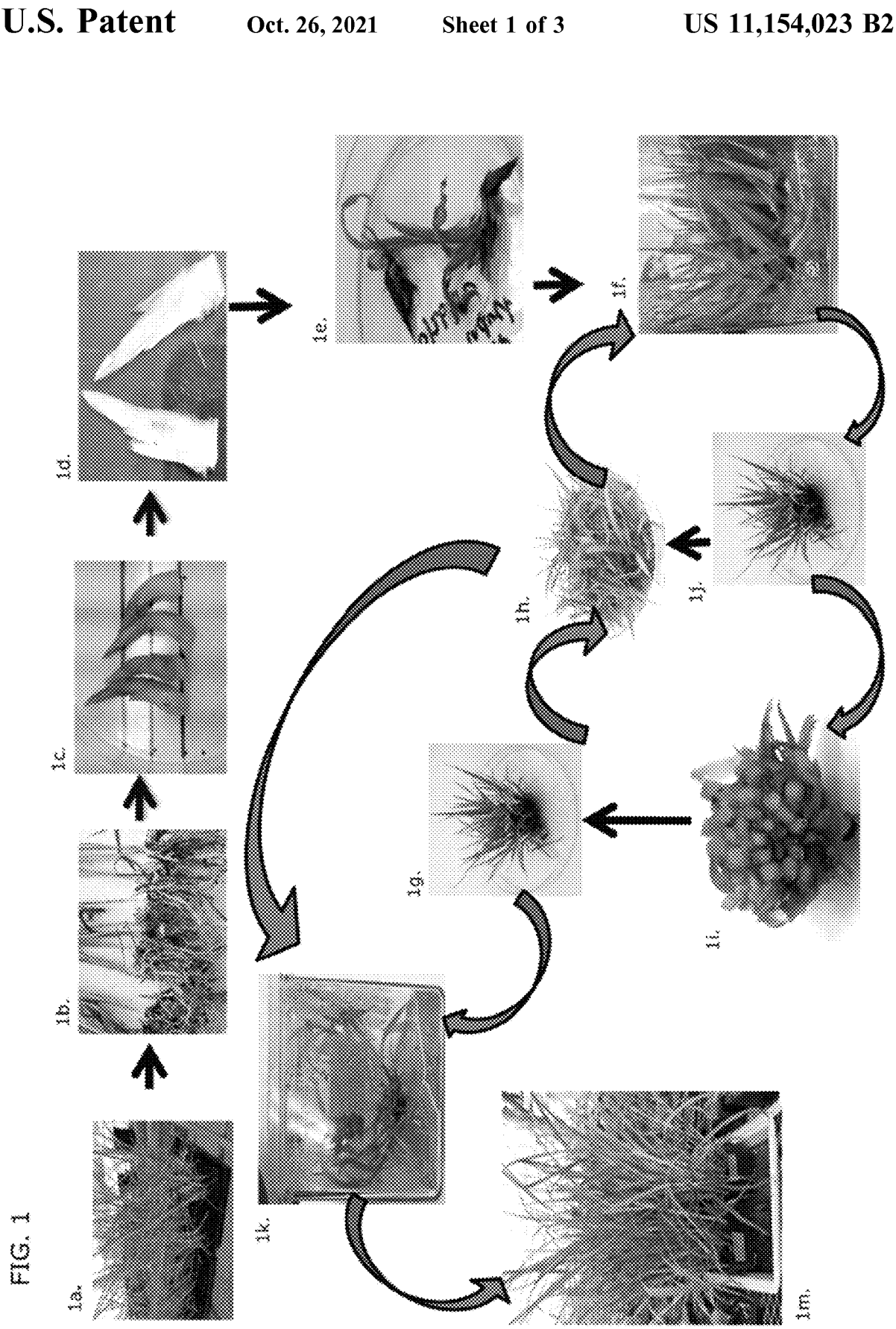
FIG. 1 shows experimental workflows followed for in vitro propagation of Miscanthus x giganteus (Giant miscanthus). 1a. Seedlings of Giant miscanthus with rhizomes purchased from a nursery; 1b. Rhizomes with immature tillers separated from soil; 1c. Immature tillers separated from Rhizomes and sterilized; 1d. longitudinally split immature tillers separated from rhizomes (LSITR); 1e. Shoot induction from LSITR; 1f. Multiple in vitro tillers induction; 1g. Isolated individual in vitro tillers; 1h. iterative cycle of in vitro multiple tillers induction; 1i. CSSSP; 1j. iterative cycle of in vitro multiple tillers induction; 1k. rooting of individual in vitro shoots (IIS)/and small clusters (sCMIT); and 1m. In vitro regenerated and micro propagated Giant Miscanthus plants well established and growing profusely in the greenhouse.

The present invention provides a novel in vitro system for rapid, efficient, robust, and cost-effective mass propagation of Miscanthus x giganteus (Giant miscanthus) using in vitro tillers or cluster of multiple in vitro shoots (CMIT) and preparation of the in vitro tillers and the CMIT. This invention is based on a surprising discovery of a cluster of stem segments containing shoot primordia (CSSSP) and its in vitro tillering power.

While few literatures described systems of direct in vitro tillering from nodal segment of Giant miscanthus, the used of longitudinally split immature tiller separated from a rhizome (LSITR) to induce shoots and orchestrate an iterative cycle of in vitro multiple tillers production from CMIT is novel. The clear potential of robustness from other systems described in the literature is not well articulated. Most of these other systems for in vitro propagation of Giant miscanthus have an inflorescence-based high quality embryogenic callus stage which is a costly, less efficient, less reproducible and cumbersome regeneration step. The iterate cycle of multiple in vitro tillering can be incredibly supported and maintained. The iterative cycle of multiple in vitro tillering represents a novel and very robust alternative approach for asexually propagating Giant miscanthus. Furthermore, these iterative cycles have the potential to achieve an unprecedented production of a massive number of high quality, regenerate *Miscanthus* x *giganteus* plantlets in a more efficient end cost-effective manner. Therefore, this production system is more effective than the conventional ex vitro rhizome-based approach.

A longitudinally split immature tiller separated from a rhizome (LSITR) of *Miscanthus* x *giganteus* (Giant miscanthus) is provided. The term "longitudinally split immature tiller separated from a rhizome (LSITR)" used herein refers to healthy and normal young tillers selected and harvested from rhizomes of *Giant miscanthus*.

A cluster of multiple in vitro shoots (CMIT) of *Miscanthus* x *giganteus* (Giant miscanthus) is provided. The term "cluster of multiple in vitro shoots (CMIT)" used herein refers to multiple in vitro shoots arranged in a form of a single morphological structure of *Giant miscanthus*.

A cluster of stem segments containing shoot primordia (CSSSP) of *Miscanthus* x *giganteus* (Giant miscanthus) is provided. The term "cluster of stem segments containing shoot primordia (CSSSP)" used herein refers to a cluster of multiple in vitro shoots of Giant Miscanthus where about three quarter of each shoot within the cluster has been removed to preserve the basal portion rich in minuscules shoot primordia.

An induced individual shoots (IIS) of *Miscanthus* x *giganteus* (Giant miscanthus) is provided. The term "induced individual shoots (IIS)" used herein refers to a new organ genic or shoot structure formed as a result of culturing a longitudinally split immature tiller separated from a rhizome of Giant Miscanthus (LSITR) in a direct shoot induction medium (DSIM) and incubating under controlled environmental growing conditions, for example, temperature set at about 26-30° C. (e.g., 28° C.), humidity at about 70-90% (e.g., 80%), and about 15-17 hours (e.g., 16 hours) of light and about 9-10 hours (e.g. 6 hours) of dark photoperiod regime must remain constant in the environmentally controlled plant growth chamber throughout the one month incubating period for induction of IIS.

Multiple in vitro tillers of *Miscanthus* x *giganteus* (Giant miscanthus) are provided. The term "multiple in vitro tillers" used herein refers to multiple In vitro organogenic shoot structures of *Giant miscanthus*.

The term "tillering power" used herein refers to the regeneration capability of a cluster of stem segments containing shoot primordia (CSSSP) to fully recover into a cluster of multiple in vitro shoots (CMIT) under culturing and incubating conditions, for example, temperature set at about 26-30° C. (e.g., 28° C.), humidity at about 70-90% (e.g., 80%), and about 15-17 hours (e.g., 16 hours) of light and about 9-10 hours (e.g., 8 hours) of dark photoperiod regime must remain constant in the environmentally controlled plant growth chamber throughout the one month incubating period for favoring tillering induction and maintenance.

The term "direct shoot induction medium (DSIM)" used herein refers to a culture medium prepared from grade chemicals with strong capacity to favor shoot induction from cultured longitudinally split immature tiller separated from a rhizome of *Giant Miscanthus* (LSITR). DSIM may comprise maltose, 6-benzylaminopureine (BAP) and α-naphthaleneacetic Acid (NAA). The DSIM may comprise about 10-30 μM BAP and about 0.8-1.2 μM NAA. In one embodiment, the DSIM may comprise about 10-15 μM BAP and about 0.8-1.2 μM NAA. In another embodiment, the DSIM may comprise about 23-27 μM BAP and about 0.8-1.2 μM NAA. The DSIM may further comprise maltose. For example, the DSIM may comprise about 20-40 g/L, about 10-30 μM BAP and about 0.8-1.2 μM NAA. In one embodiment, the DSIM may comprise about 20-40 g/L, about 10-15 μM BAP and about 0.8-1.2 μM NAA. In another embodiment, the DSIM may comprise about 20-40 g/L, about 23-27 μM BAP and about 0.8-1.2 μM NAA.

The present invention provides a method of generating a CMIT of Giant miscanthus. The CMIT preparation method comprises incubating a LSITR of Giant miscanthus in a DSIM such that the LSITR develops IIS, excising each of the IIS from its base on the LSITR, and incubating each of the excised IIS in the DSIM. As a result, a CMIT is generated.

The present invention also provides a method of generating a CSSSP of Giant miscanthus. The CSSSP preparation method comprises incubating the CMIT in a DSIM so that the CMIT develops multiple in vitro tillers and removing the multiple in vitro tillers from the CMIT so that the CSSSP is generated. Nodes located near the base of each removed in vitro tiller remain within the CSSSP. The multiple in vitro tillers may comprise at least 30 in vitro tillers. As a result, a CSSSP is generated.

The present invention further provides another CSSSP preparation method. This method comprises incubating a LSITR of Giant miscanthus in a DSIM so that the LSITR develops one or more IIS, excising each of the IIS from its base on the LSITR, incubating each of the excised IIS in the DSIM so that a CMIT is generated, incubating the CMIT in the DSIM so that the CMIT develops multiple in vitro tillers, and removing the multiple in vitro tillers from the CMIT to generate the CSSSP. Nodes located near the base of each removed in vitro tiller remain within the CSSSP. The multiple in vitro tillers may comprise at least 30 in vitro tillers. As a result, a CSSSP is generated.

The present invention further provides another CMIT preparation method. The method comprises incubating a CSSSP of Giant miscanthus in a DSIM so that the CMIT is generated. As a result, a CMIT is generated.

The present invention further provides a method of producing multiple in vitro tillers of Giant miscanthus. The method comprises incubating a CMIT in a DSIM so that the CMIT develops multiple in vitro tillers. The method may further comprise isolating a single in vitro tiller from the multiple in vitro tillers and incubating the single in vitro tiller in the DSIM so that the single in vitro tiller develops multiple in vitro tillers. As a result, multiple in vitro tillers of Giant miscanthus are produced.

The present invention further provides another method of producing multiple in vitro tillers of Giant miscanthus. The method comprises fragmenting a CSSSP into small clusters of stem segments and incubating each of the small clusters in a DSIM so that each of the small clusters of stem segments develops multiple in vitro tillers. Each of the small clusters may comprise at least 5 stem segments. As a result, multiple in vitro tillers of Giant miscanthus are produced.

The present invention further provides a method of propagating Giant miscanthus. The method comprises incubating the in vitro tiller of Giant miscanthus of the present invention in a rooting medium so that an in vitro rooted *Giant miscanthus* plantlet is generated and planting the in vitro rooted plantlet into soil.

The present invention further provides another method of propagating Giant miscanthus. The method comprises incubating the CMIT of the present invention in a rooting medium so that an in vitro rooted Giant miscanthus plantlet is generated and planting the in vitro rooted plantlet into soil.

The rooting medium (RM) may comprise maltose, NAA, phytagel, and vancomycin. For example, the RM may comprise maltose at about 20-40 g/L, NAA at about 1.9-2.3 μM, phytagel at about 2.0-2.5 g/L and vancomycin at about 50-60 μM. The RM may further comprise a medium such as MS basal medium. The MS basal medium may comprise 1650 mg/L ammonium nitrate, 6.2 mg/L boric acid, 332.2 mg/L calcium chloride (anhydrous), 0.025 mg/L cobalt chloride.6H2O, 0.025 mg/L cupric sulfate.5H2O, 37.26 mg/L Na2EDTA.2H2O, 27.8 mg/L ferrous sulfate.7H2O; 180.7 mg/L magnesium sulfate (anhydrous), 16.9 mg/L manganese sulfate.H2O, 0.25 mg/L molybdic acid (sodium salt).2H2O, 0.83 mg/L potassium iodide, 1900 mg/L potassium nitrate, 170 mg/L potassium phosphate (monobasic), 8.6 mg/L zinc sulfate.7H2O, 2.0 mg/L glycine (free base), 100 mg/L myo-inositol, 0.5 mg/L nicotinic acid (free acid), 0.5 mg/L pyridoxine.HCl and 0.1 mg/L thiamine.HCl. The rooting medium may have a pH of 5-6, for example, about 5.7.

Example 1

Discovery of CSSSP and its In Vitro Tillering Power

The in vitro morphological structure named CSSSP (FIG. 1*i*.) originates from in vitro tillers of in vitro plantlets elongated from direct shoot induction (FIG. 1*e*.) from LSITR of *Miscanthus* x *giganteus* (Giant miscanthus) that was commercially acquired and subsequently established in the greenhouse for about four months (FIG. 1*a*.).

Figure 2:
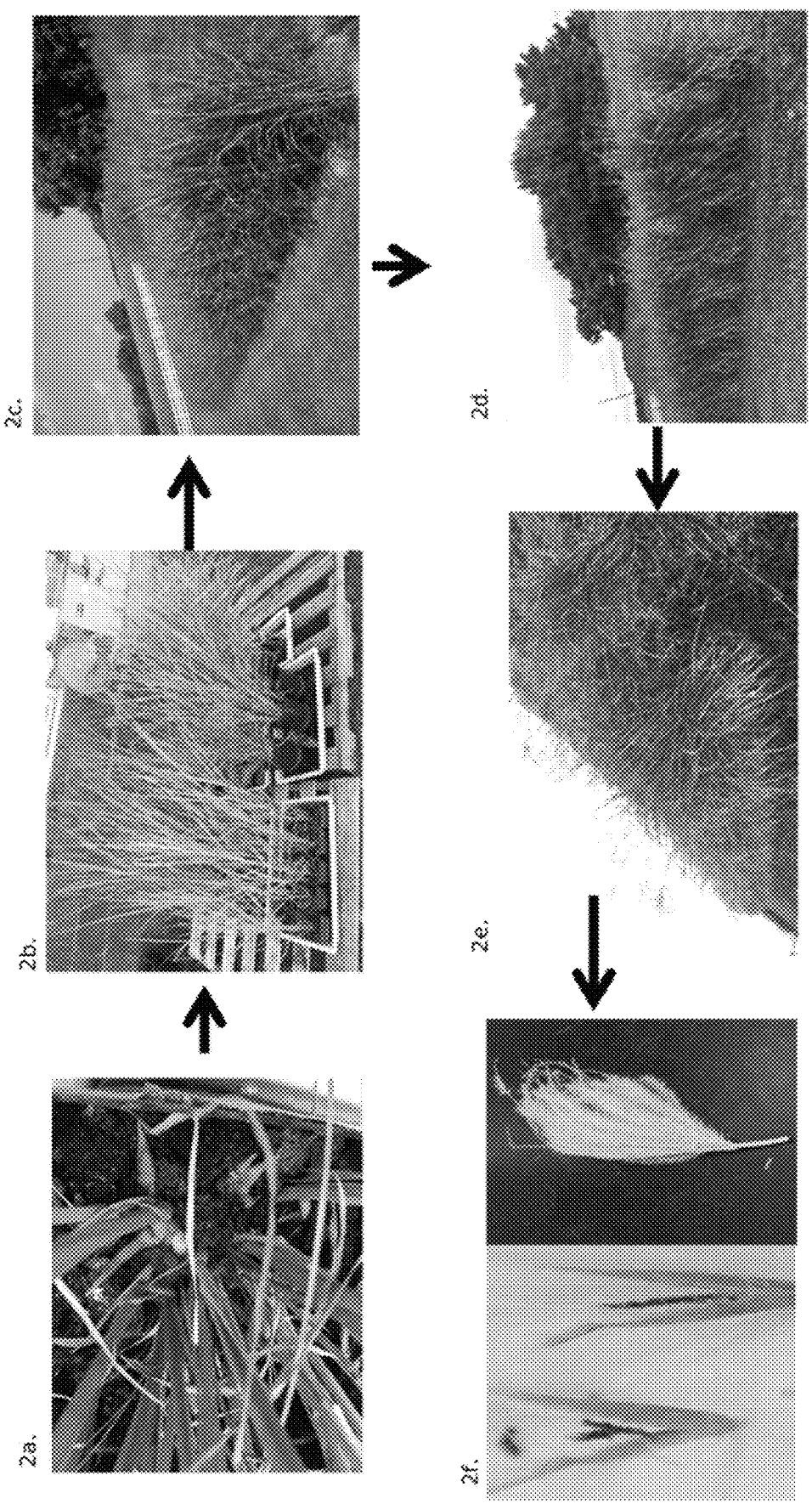
FIG. 2 shows field establishment to test adaptability and evaluate yield potential of in vitro regenerated and propagated Miscanthus x giganteus (Giant miscanthus). 2a. Greenhouse established Giant miscanthus seedlings prior to transplantation in the field showing developed multiple immature tillers (IT) which will grow to mature tillers and boost the overall biomass yield of in vitro regenerated; 2b. In vitro regenerated and micro propagated Giant Miscanthus plants well acclimatized in the greenhouse prior to field establishment; 2c. In vitro regenerated and micro propagated Giant miscanthus plants successfully established in the field two months after planting; 2d. In vitro regenerated and micro propagated Giant miscanthus plants successfully established in the field six months after panting; 2e. In vitro regenerated and micro propagated Giant miscanthus plants successfully established in the field at flowering stage six months after planting; and 2f. Infertile spikelet, typical of Giant miscanthus isolated from matured inflorescences of field established in vitro regenerated plants eight months after planting.
Figure 3:
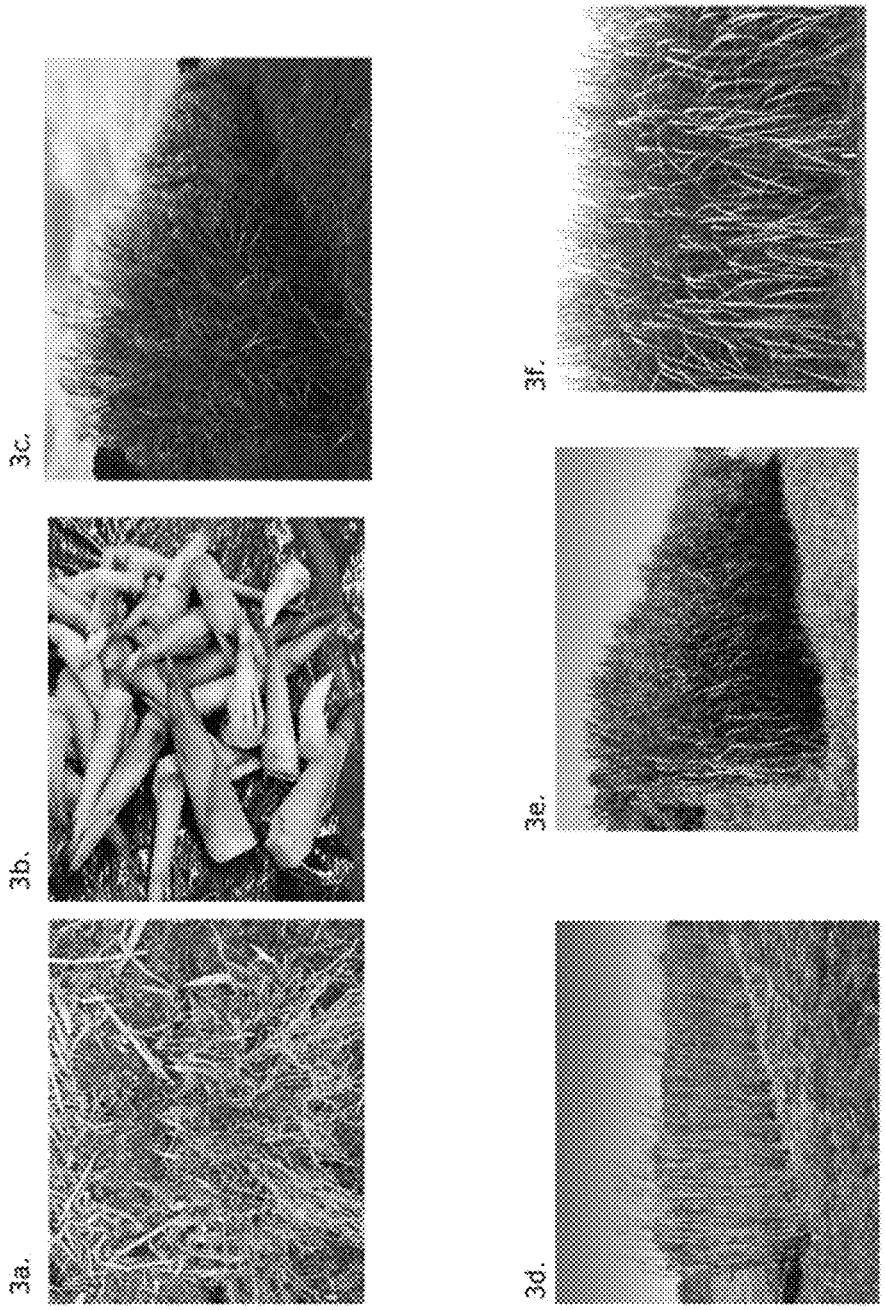
FIG. 3 shows field establishment to test adaptability and evaluate yield potential in vitro regenerated and propagated Miscanthus x giganteus (Giant miscanthus) according to yet another embodiment of the present invention. 3a. Two-year-old field grown in vitro regenerated, and micro propagated Giant Miscanthus plants showing healthy underground tillers, profuse root system and rhizomes; 3b. Clean and normal tillers harvested from rhizomes of two-year-old field grown in vitro regenerated, and micro propagated Giant Miscanthus plants; 3c. Flowering of two-year-old field grown of in vitro regenerated, and micro propagated Giant miscanthus plants; 3d. Dried biomass from two-year-old field grown of in vitro regenerated, and micro propagated Giant miscanthus plants; 3e. Third year field grown of in vitro regenerated, and micro propagated Giant miscanthus plants; and 3f. Comparison of third-year field grown of in vitro regenerated, and micro propagated Giant miscanthus plants and mother plants showing no variability in their growth vigor.

CSSSP was discovered by a surprising observation which deviated from the original research hypothesis. The initial research hypothesis was a motivation based on a previous work in switchgrass, a related species to Giant miscanthus, on the successful induction of axenic flowers from top nodal segments of tillers of greenhouse established plants. At a starting point, we basically designed an experiment to orchestrate transferability of the in vitro system for the induction of axenic flowers from switchgrass. To that effect, top nodal segments from commercially acquired and greenhouse established Giant miscanthus were split and cultured on inflorescence induction medium supplemented with a cytokinin and an auxin modified from Alexandrova et al. (1996). The inflorescence induction medium contained a Murashige & Skoog (MS) basal medium with vitamins (Murashige and Skoog 1962) purchased from PhytoTechnology Laboratories), 30 g/L maltose, 12.5 or 25 μM 6-Benzylaminopureine (BAP) and 1.08 mM α-Naphthaleneacetic Acid (NAA). The composition of the MS basal medium is in (mg/L): 1650, ammonium nitrate; 6.2, boric acid; 332.2, calcium chloride anhydrous; 0.025, cobalt chloride.6H2O; 0.025, cupric sulfate.5H2O; 37.26, Na2EDTA.2H2O; 27.8, ferrous sulfate.7H2O; 180.7, magnesium sulfate, anhydrous; 16.9, manganese Sulfate.H2O; 0.25, molybdic acid (sodium salt).2H2O; 0.83, potassium iodide; 1900, potassium nitrate; 170, potassium phosphate, monobasic; 8.6, zinc sulfate.7H2O; 2.0, glycine (free base); 100, myo-inositol; 0.5, nicotinic acid (free add); 0.5, pyridoxine.HCl; 0.1, thiamine.HCl, Phytagel (2.2 g/L) was used as a gelling agent. The pH of the media was adjusted to 5.7, and the media was sterilized by autoclaving and poured into sterile petri dishes. For all in vitro manipulations described here, plant growth chamber optimum incubation conditions for all cultured were: temperature: 28° C., relative humidity: 80%, photoperiod; 16 hr. light/8 hr dark regime except otherwise stated. Surprisingly, incubated explants of the nodal segments of Giant miscanthus resulted in direct shoot induction (FIG. 1*e*.) rather than axenic flower as originally expected. But this later process did not result in multiple shoots formation, and further regeneration trials using this system were discontinued. We then attempted to extend this in vitro inflorescence induction system to sterilized and longitudinally split immature tillers developing from rhizomes (LSITR) (FIG. 1*d*.). This resulted in shoot induction and subsequent elongation. Induced individual shoots (IIS) (FIG. 1*e*.) were carefully excised at the base and subcultured back into this inflorescence induction medium (IIM), later named, direct shoot induction medium (DSIM), which is MS basal medium supplemented with 30 g/L maltose, 12.5 or 25 μM 6-Benzylaminopureine (BAP) and 1.08 mM α-Naphthaleneacetic Ac id (NAA), to induce in vitro shoot organogenesis. This later process generated clusters of multiple in vitro shoots (CMIT) (FIG. *f*.) from each induced individual shoot (IIS). Each CMIT developed approximately 30 new in vitro tillers. CSSSP was derived from CMIT from which all in vitro tillers were strategically removed (FIG. 1*f*.) so that "miniscules" nodes located near the base of each in vitro tiller remain within the CSSSP which will serve as shoot primordia for next in vitro tillering upon successive culturing of the CSSSP into DSIM. In order to improve the frequency and the quality of IIS from LSITR, we tested various levels of cytokinin BAP levels (0, 12.5 or 25 μM BAP) in combination with three different ages of immature tillers comporting 1, 2 or 3 batches of leaf sheath, and various types and levels of antibiotics vancomycin hydrochloride (0, 13.5, 27, 41.5, and 54 μM) and tetracycline hydrochloride (20.8 μM or 52 μM) were included in the media to eliminate the effect of endophytes in in vitro shoot performance. However, since 54 μM vancomycin was more effective in controlling the growth of endophytic fungi in the culture media, it was then used for subsequent experiments. These later (DSIM) optimizations led to the development of an enhanced DSIM (eDSIM) (e.g., MS basal medium supplemented with 30 g/L maltose, 12.5 μM 6-Benzylaminopureine (BAP) and 1.08 μM α-Naphthaleneacetic Acid (NAA)), which proved to be very effective medium to support subsequent multiple in vitro tillering and tillering maintenance from CSSSP. Fragmentation of CSSSP into a small cluster of 5 stems segments and transferring of these fragments into (eDSIM) generated new in vitro tillers corresponding to the initial number of stem cuttings within each small CSSSP cluster. Conversely, transferring of a single in vitro tiller isolated from a CMIT to eDSIM triggered new multiple in vitro tillering to generate high quality CMIT with morphological features similar to the mother CMIT. From this point on, and efficient iterative cycles of multiple in vitro tillering from single in vitro tiller, tillers isolated from a CMIT and those originated from subsequent generation CSSSP is successfully sustained over an extended period of time (FIGS. 1*h* and 1*j*). Prior to establishing regenerated single in vitro shoot and small CMIT clusters in the greenhouse and field to evaluate performance, a Rooting Medium (RM) need to be formulated in a manner that supports high quality (healthy) root formation and proliferation and healthy growth of shoots and small CMIT clusters. Through trials and testing the levels of various nutrients, auxins, energy sources, a very effective RM was formulated. The composition of the final RM (MS basal medium supplemented 30 g/L maltose, 2.15 µM NAA and 2.2 g/L phytagel, and the pH was adjusted to 5.7, and 54 µM vancomycin) was added prior to poring the media into magenta jars. This RM has been used with a good success in inducing high quality and proliferating root system to support vigorous growth of single in vitro shoots and small CMIT clusters (FIG. 1k.). Interestingly, we also observed CMIT in RM with high frequency. Once the efficiency of this RM was demonstrated, we designed a post-flask management system to acclimatize these rooted single in vitro shoots and small CMIT clusters in the greenhouse prior to field establishment. The hardening process was as follow: Several types of potting mixes were tested for the hardening process of the rooted in vitro shoots, and we finally identified a soil mix that best supports the establishment. The "More Suitable Soil Mix" (MSSM) contains: one part sandy-loam, two-part sand, three-part peat moss, and three-part vermiculite. Four-inch square pots were filled with 350 g of this soil mix containing 0.4 g of Scotts 15-9-12 Osmocote Plus. The soil was moistened with tap water, and the in vitro rooted plantlets were transferred to the soil. Then, the plantlets were left under a dome for five to seven days until they survived in the soil. The plants were then transferred to the greenhouse and establish for about two months (FIG. 1m.). Two weeks prior to transplanting in the field, plants were placed in an open air outside the greenhouse for acclimatization and monitored (FIG. 2b.). Our data showed a 100% establishment rate for all the rooted single in vitro tillers and small CMIT clusters in the green house and the field. Under both conditions, all in vitro regenerated Giant miscanthus plants showed high tillering capacity under greenhouse conditions.

This iterative cycle of multiple in vitro tillering was supported and maintained by the well and carefully formulated (eDSIMm) which was a modification of eDSIM with a reduced auxin level. The iterative cycle of multiple in vitro tillering describing in this disclosure represent a novel and robust alternative approach for asexually propagating this important energy crop. Furthermore, this cycle has the potential to achieve an unprecedented production of a massive number of high quality, regenerate *Miscanthus* x *giganteus* plantlets in a more efficient and cost-effective manner. Field-established plants were weeded only once (one-month) after planting, and subsequent weeding were not needed due to profuse growth of the established plants which developed many young tillers.

Therefore, this production system is more effective than the conventional ex vitro rhizome-based approach. In our laboratory, observations over three years brought us to propose a formula that depicts the CSSSP's in vitro tillering power.

PT: Power of in vitro tillering for $CSSSP=m30^n$

Where 30: is the approximate number of individual tillers or shoots generated from a single cluster of multiple in vitro tilers (CMIT) and n: the number of the iterative cycle of in vitro propagation, m: number of the Induced individual shoots (IIS). PT formula has been validated in our laboratory and this variable (m) is extremely critical to attain the desired stage of CSSSP which is triggered by the vigor, health, age and texture of the IIS. The quality of IIS which are competent to induce (CMIT) depend on the morphological stage of the immature tillers at the time it is separated from the rhizomes on the mother plants prior to longitudinal split and cultured on the eDSIM for CMIT induction. Under optimal conditions for IIS and CMIT induction, CSSSP with potential to perpetrate the iterative cycles of multiple in vitro tillering is generated. On the assumption that m=1, and n=1, PT will be equal to 30, which is equivalent to the number of in vitro tillers in a CMIT. If m=2, and n=2, $PT=2\times30^2$, $PT=2\times30\times30=1800$ in vitro tillers at the second iterative multiple in vitro tillering. As the number of IIS and iteration increase, a significant number of in vitro tillers are produced, such in vitro tillers have shown to root efficiently in our formulated RM and exhibited a 100% greenhouse acclimatization and field establishment rate.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

The invention claimed is:

1. A method of generating a cluster of stem segments containing shoot primordia (CSSSP) of *Miscanthus* x *giganteus* (Giant miscanthus), comprising
    (a) incubating a longitudinally split immature tiller separated from a rhizome (LSITR) of Giant miscanthus in a direct shoot induction medium (DSIM), whereby the LSITR develops one or more induced individual shoots (IIS),
    (b) excising each of the IIS from its base on the LSITR,
    (c) incubating each of the excised IIS in the DSIM, whereby a cluster of multiple in vitro shoots (CMIT) is generated,
    (d) incubating the CMIT in the DSIM, whereby the CMIT develops multiple in vitro tillers, and
    (e) removing the multiple in vitro tillers from the CMIT, whereby the CSSSP is generated, wherein nodes located near the base of each removed in vitro tiller remain within the CSSSP.

2. The method of claim 1, further comprising
    (a) isolating a single in vitro tiller from the multiple in vitro tillers, and
    (b) incubating the single in vitro tiller in the DSIM, whereby the single in vitro tiller develops multiple in vitro tillers.

3. The method of claim 1, further comprising
    (a) fragmenting the CSSSP into small clusters of stem segments, and
    (b) incubating each of the small clusters in a direct shoot induction medium (DSIM), whereby each of the small clusters of stem segments develops multiple in vitro tillers.

4. The method of claim 3, wherein each of the small clusters comprises at least 5 stem segments.

5. The method of claim 1, wherein the DSIM comprises maltose, 6-benzylaminopureine (BAP) and α-naphthaleneacetic Acid (NAA).

6. The method of claim 1, further comprising
    (a) incubating the in vitro tiller in a rooting medium, whereby an in vitro rooted Giant miscanthus plantlet is generated, and
    (b) planting the in vitro rooted plantlet into soil, whereby a Giant miscanthus plant is generated.

7. The method of claim 1, further comprising
    (a) incubating the CMIT in a rooting medium, whereby an in vitro rooted Giant miscanthus plantlet is generated, and (b) planting the in vitro rooted plantlet into soil, whereby a Giant miscanthus plant is generated.

8. The method of claim 6, wherein the rooting medium comprises maltose, α-naphthaleneacetic Acid (NAA), phytagel, and vancomycin.

9. The method of claim 6, wherein the rooting medium has a pH of 5-6.

10. The method of claim 1, wherein the multiple in vitro tillers comprise at least 30 in vitro tillers.

11. The method of claim 1, further comprising incubating the CSSSP in the DSIM, whereby the CMIT is amplified.

* * * * *